United States Patent
Aiache et al.

(12) 
(10) Patent No.: US 6,210,711 B1
(45) Date of Patent: Apr. 3, 2001

(54) EFFERVESCENT MICROSPHERES AND METHOD FOR MAKING THEM

(75) Inventors: Jean-Marc Aiache; Pascale Gauthier, both of Clermont-Ferrand; Joël Bougaret, Lanta, all of (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 09/341,780

(22) PCT Filed: Jan. 15, 1998

(86) PCT No.: PCT/FR98/00070

§ 371 Date: Aug. 13, 1999

§ 102(e) Date: Aug. 13, 1999

(87) PCT Pub. No.: WO98/31342

PCT Pub. Date: Jul. 23, 1998

(30) Foreign Application Priority Data

Jan. 16, 1997 (FR) .................................................. 97 00394

(51) Int. Cl.$^7$ ................................ A61K 9/46; A61K 9/16
(52) U.S. Cl. ........................... 424/466; 424/489; 424/490
(58) Field of Search ..................................... 424/466, 489, 424/490

(56) References Cited

U.S. PATENT DOCUMENTS 5,792,473 * 8/1998 Gergely et al. ...................... 424/466

FOREIGN PATENT DOCUMENTS

0415326 A1  3/1991  (EP) .
0670160 A1  9/1995  (EP) .

* cited by examiner

*Primary Examiner*—James M. Spear
(74) *Attorney, Agent, or Firm*—The Firm of Hueschen and Sage

(57) ABSTRACT

The invention concerns multilayer microspheres containing an acid substance, a basic substance, and a water-soluble isolating agent which, when it dissolves in water, after almost instant effervescence, brings about a homogeneous dispersion of active principal(s) which is present in the acid and basic substances. The invention also concerns a method for preparing such microspheres by rotational granulation on a fluid air bed associated with a system of tangential spraying of the wetting liquid.

22 Claims, No Drawings

EFFERVESCENT MICROSPHERES AND METHOD FOR MAKING THEM

The present application is a U.S. National Application filed under 35 USC 371 of PCT/FR98/00070, filed Jan. 15, 1998 based upon French application Ser. No. 97/00394 filed Jan. 16, 1997.

The present invention relates to multilayer effervescent microspheres and to a process for preparing such microspheres.

The term "microsphere" will be intended to refer to microgranules formed of a support material consisting of a matrix in which the active principle(s), to which auxiliary substances are optionally added, is (are) dispersed. In accordance with the European Pharmacopea monograph on spheres, microspheres have an average diameter of less than 1.0 mm and greater than or equal to 1.0 $\mu$m. They are generally intended for oral or parenteral administration and are used either as constituents of pharmaceutical form, such as tablets, or in their natural form combined or otherwise with other excipients, and distributed or otherwise in unit doses, such as sachets, gel-capsules or powder for injectable preparation.

The effervescent forms for pharmaceutical use described in the prior art exclusively comprise granules and tablets obtained by compressing these granules.

These effervescent forms are intended to be dispersed in water before absorption. Their breakdown is ensured by a release of carbon dioxide resulting from the action of an acid—generally an organic acid, citric acid being the one most commonly used—on a base—generally a carbonate such as sodium bicarbonate, potassium bicarbonate, lithium bicarbonate, calcium carbonate, magnesium carbonate or lysine carbonate to avoid the introduction of sodium.

The known effervescent forms also comprise diluent adjuvants (generally sugars), binders, sweeteners and flavorings.

Most of the standard processes for preparing effervescent forms comprise a step of granulating powder, either via a wet route or via a dry route.

Despite the difficulties present therein, wet granulation is the method most commonly used.

According to a first variant described in the "Journal of Pharmaceutical Sciences, 1964, 53, 1524–25", the acidic and basic substances, the active principle(s) and the adjuvants are mixed together in a fluidized air bed. The granulation is initiated by spraying the powder with distilled water or an aqueous diphosphate solution. The water thus sprayed on initiates an effervescence reaction which allows the creation of bonds between the particles of powder. The water is sprayed on until the granules reach the desired size. The drawback of this method is the lack of reproducibility of the results due to poor control of the effervescence reaction.

Patent application EP 673,644 proposes to control the effervescence reaction of the process described in the above reference, by maintaining the moisture content of the air supplied to the fluidized air bed between 0 and 1 g/m$^3$, on the one hand, and by evaporating the nebulized water at the surface of the granules being formed while at the same time continuing the spraying with water, on the other hand. The granules are dried once the desired size has been reached. This application describes the use of water or of an aqueous-alcoholic mixture as wetting liquid.

According to a second variant described in patent EP 369,228, the acidic and basic substances are granulated separately and then mixed together after drying. This process is expensive to implement.

In patent application WO 96/19982 which describes a process for preparing effervescent compositions containing ibuprofen, the granulation step concerns only the alkaline substance. According to this process, the granulated alkaline substance is mixed with pulverulent ibuprofen.

Dry granulation includes two phases: compression of the powder and grinding-screening of the powder tablets. This process is of little interest for the preparation of effervescent forms due to the chemical nature of the products inducing bonding phenomena.

Patent FR 2,552,308 describes a process for preparing an effervescent mixture by a method which does not involve a granulation step.

According to the described process, the effervescent mixture contains at least one crystalline solid organic acid and at least one carbonate releasing $CO_2$ in the reaction with the organic acid and is characterized in that the acid crystals bear a coating containing calcium carbonate which adheres to the surface of the acid crystals by means of the bonding layer formed by partial react-on of the calcium carbonate of the coating with a surface layer of each acid crystal. The mixture is prepared by heating the organic acid in ethanol and water to about 60° C. in a mixer at a pressure of about 0.1 bar or less and by introducing the calcium carbonate which is left to react until the pressure has risen to about 0.9 bar.

The present invention relates to multilayer effervescent microspheres containing an acidic substance, a basic substance and a water-soluble isolating agent whose dissolution in water leads, after almost immediate effervescence, to a solution or a homogeneous dispersion of active principle.

According to a first variant, the water-soluble isolating agent is dispersed in the entire bulk of each microsphere, the latter having a two-layer structure: a layer of acidic substance in which is dispersed the water-soluble isolating agent and a layer of alkaline substance in which is dispersed the water-soluble isolating agent.

According to a second variant, the water-soluble isolating agent is in the form of a thin film separating the acidic and alkaline substances. In this case, each microsphere has a three-layer structure: a layer of acidic substance and a layer of alkaline substance separated by a layer of water-soluble isolating agent.

Whether the microspheres have a two-layer or three-layer structure, the water-soluble isolating agent serves two purposes; it acts as a binder and as an isolating barrier intended to avoid an effervescence reaction between the alkaline substance and the acidic substance during the preparation process but also during storage of the microspheres, irrespective of the storage conditions.

The water-soluble isolating agent is chosen from polyvinylpyrrolidone, hydroxypropyl cellulose, methyl cellulose, lactose and sucrose.

The present invention also relates to a process for preparing the effervescent microspheres described above using the method of rotary granulation in a fluidized air bed.

The advantage of rotary granulation applied to these effervescent compositions is the continuous linking of the operations in one and the same chamber which, as a result of the components used and certain precautions taken, induces no effervescence. Furthermore, this rotary granulation technique allows the relative proportions of the various compounds to be modified, in particular the relative molar proportions of the acidic and basic fractions.

Specifically, the process according to the invention makes it possible advantageously to obtain effervescent forms whose relative proportion of alkaline and acidic fractions is less than the stoichiometric proportion implemented in the prior art for effervescent tablets manufactured by the granulation method, without the quality of the effervescence being adversely affected.

In particular, the relative proportion of the alkaline and acidic fractions implemented in the context of the process according to the invention is less than 0.6, in particular less than 0.25.

All the steps of the process according to the invention are carried out under atmospheric pressure, without any specific dehydration system or any specific precautions.

The apparatus used to carry out the process for preparing the effervescent microspheres is, for example, apparatus constructed by the company Glatt, onto which a rotor tank is fitted.

Such an item of apparatus is described in patent EP 0,505,319, which we include, by way of reference, in the present application.

A subject of the present invention is, firstly, a process for preparing effervescent microspheres which have a two-layer structure according to the first variant described above.

Said process is performed by rotary granulation in a fluidized air bed combined with a system for spraying powder and a system for the tangential spraying of wetting liquid. The process comprises two continuous steps, a first step of spheronization of microspheres using a powder A and a second step of spheronization of a powder B on the microspheres of powder A, one of the powders A and B being acidic and the other alkaline and it being possible for each of them to contain or consist of one or more active principles.

During the first spheronization, the powder A is placed in the moving rotary granulation tank and suspended in the air bed. The components of the powder A are mixed together for five minutes and the air inlet temperature is stabilized to a temperature $T_o$.

The powder A thus blended is sprayed with a wetting liquid containing the water-soluble isolating agent. The microspheres of powder A obtained are dried by bringing the air inlet temperature to Ts and are then optionally screened using a 1000 $\mu$m screen. During the second spheronization, the air inlet temperature is brought to To. The powder B and the wetting liquid containing the water-soluble isolating agent are then simultaneously sprayed onto the dried powder A microspheres obtained previously. The powder B is sprayed by means of the powder spraying system installed on the Glatt apparatus. The two-layer microspheres obtained are dried by bringing the air inlet temperature to Ts. After drying, the microspheres must be packaged quickly, but a small amount of moisture uptake does not harm the storage.

During the two spheronizations, the wetting liquid containing the water-soluble isolating agent is the same, for example polyvinylpyrrolidone (PVP) dissolved in an alcohol or an aqueous-alcoholic mixture, in particular PVP dissolved to 4% by weight in ethanol at 60% by volume.

The two-layer microspheres obtained according to the process of the invention have an average particle size of between 20 and 500 $\mu$m.

A subject of the present invention is also a process for preparing effervescent microspheres which have a three-layer structure according to the second variant described above.

Said process is performed according to the method of rotary granulation in a fluidized air bed combined with a system for the tangential spraying of wetting liquid.

The process comprises three continuous steps, a first step of spheronization of microspheres using a powder A, a second step of spheronization of a water-soluble isolating agent on the microspheres of powder A, and then a third step of spheronization of a powder B on the microspheres A protected with a film of water-soluble isolating agent, one of the powders A and B being acidic and the other alkaline and it being possible for each of them to contain or consist of one or more active principles.

During the first spheronization, the powder A containing an added binder, for example PVP, is placed in the moving tank and suspended in the air bed. The components of the powder A are mixed together for five minutes and the air inlet temperature is stabilized to To. The powder A thus blended is sprayed with a wetting liquid. The microspheres of powder A obtained are dried by bringing the air inlet temperature to Ts. During the second spheronization, the air inlet temperature is brought to To. The water-soluble isolating agent is added directly to the tank and the wetting liquid sprayed until microspheres of powder A which are coated with a film of water-soluble isolating agent are obtained, and are dried by bringing the air inlet temperature to Ts. After drying, the coated microspheres are screened and the powder B is then added directly to the rotary granulation tank when the air inlet temperature has stabilized at To. The three-layer microspheres are obtained by spraying the preceding microspheres with a wetting liquid. The three-layer microspheres obtained are dried by bringing the air inlet temperature to Ts. After drying, the microspheres must be packaged quickly, but a small amount of moisture uptake does not harm the storage.

During the first two steps, the wetting liquid is, for example, an aqueous-alcoholic solution, in particular ethanol at 60% by volume. During the final step, the water-soluble isolating agent can be introduced by means of the powder B, in which case the wetting liquid used will be the same as during the first two steps, or alternatively the isolating agent is introduced by means of the wetting liquid, which will be an alcoholic or aqueous-alcoholic solution containing the isolating agent, for example PVP dissolved to 4% by weight in ethanol at 60% by volume.

The three-layer microspheres obtained according to the process of the invention have an average particle size of between 200 and 1000 $\mu$m.

According to the process for manufacturing microspheres, whether they are two-layer or three-layer microspheres, the powder of alkaline nature contains a sodium bicarbonate or any other carbonate usually used in the preparation of effervescent forms, such as lithium hydrogen carbonate, monosodium carbonate, lithium glycine carbonate, monopotassium carbonate, calcium carbonate, magnesium carbonate; one or more active principles if the latter have alkaline properties; whereas the powder of acidic nature contains an organic acid, for example citric acid or a compound used as active principle, for example ascorbic acid, acetylleucine and/or one or more active principles if the latter have acidic properties.

The acidic and alkaline powders can also contain a diluent, for example lactose or Glucidex; flavorings and sweeteners, for example orange flavoring, citric acid, sodium saccharinate; various excipients.

According to one embodiment of the invention, the powder A is of alkaline nature and the powder B is of acidic nature.

According to another embodiment of the invention, the powder B is of alkaline nature and the powder A of acidic nature.

The wetting liquid is sprayed by means of a nozzle 1.2 mm in diameter, at an average flow rate of between 10 and 30 g/min. The air inlet temperature of the fluidized bed is between 55 and 650C during the spheronization steps (To) and between 75 and 85° C. during the drying phases (Ts).

The microspheres obtained according to the process of the invention contain 5 to 75% of alkaline substance, 10 to 75% of acidic substance, 3 to 15% of water-soluble isolating agent, 5 to 50% of diluent and 1 to 30% of flavorings and sweeteners.

The relative humidity of the microspheres obtained according to the process of the invention, measured for fifteen minutes by the infrared balance method at 90° C., is between 1 and 2% at the rotary granulation tank outlet.

The overall yield for the process is calculated from the fraction of particles smaller than 2500 $\mu$m in size, the working yield of the spheres corresponds to the fraction of particles between 200 and 1000 $\mu$m, for the process for preparing three-layer microspheres, between 20 and 500 $\mu$m for the process for preparing two-layer microspheres.

The feasibility of the process according to the invention is evaluated according to the ease with which the microspheres are obtained, the speed of production of a batch and the yield for each step.

Analysis of the batches includes particle size analysis of a sample of 100 g of spheres by the superimposed screens method (sample obtained from the total fraction of a batch), after which a morphological study of the microspheres obtained, relating to the overall appearance, sphericity, cohesion and uniformity of the particles, is carried out by examination with a binocular magnifying glass.

According to one variant of the invention, the two-layer or three-layer effervescent microspheres are manufactured by the mounting technique combined with a system for the tangential spraying of wetting liquid. The powder A and the powder B can be mounted successively on spheres of active principle coated with water-soluble isolating agent, or on neutral spheres.

The examples which follow illustrate the invention without limiting its scope.

The percentages are expressed on a weight basis.

EXAMPLE 1

Two-layer effervescent microspheres containing ascorbic acid (vitamin C)

Alkaline microspheres are prepared, on which is deposited the acidic active principle (vitamin C).

The table below gives the details of the formulation used.

| FORMULATION | COMPONENT | PERCENTAGE |
|---|---|---|
| Powder A | | |
| Alkaline compound | Sodium bicarbonate | 20% |
| Diluent | Lactose | 6% |
| Sweetener | Glucidex 6 ® | 6% |
| Powder B | | |
| Acidic compound Active principle | Ascorbic acid | 50% |
| Flavoring | Orange flavoring | 1% |
| Sweeteners | Sodium saccharinate | 0.3% |
| | Glucidex 6 ® | 6.35% |
| Diluent | Lactose | 6.35% |

The wetting liquid used during the two successive rotary granulations is an aqueous-alcoholic PVP solution containing 4% PVP in ethanol at 60% by volume.

This mixture is sprayed at an average flow rate of 25 grams per minute.

In this formulation, the lactose is combined in equal part with Glucidex 60, although it is possible to use lactose alone.

The powder formulations A and B were prepared on batches of variable size of 1000 to 5000 g with, depending on the case, use of equipment from the company Glatt.

The effervescent spheres obtained have a fairly uniform appearance and a majority particle size of fractions between 200 and 500 $\mu$m. The relative humidity is 1.6% at the rotary granulation tank outlet.

EXAMPLE 2

Two-layer effervescent microspheres containing acetylleucine

Alkaline microspheres are prepared, on which is deposited the acidic active principle (acetylleucine) under the same conditions as in Example 1.

The table below gives the details of the formulation used.

| FORMULATION | COMPONENT | PERCENTAGE |
|---|---|---|
| Powder A | | |
| Alkaline compound | Sodium bicarbonate | 20% |
| Diluent | Lactose | 9.85% |
| Powder B | | |
| Acidic compound Active principle | Acetylleucine | 50% |
| Flavoring | Orange flavoring | 1% |
| Sweetener | Sodium saccharinate | 0.3% |
| Diluent | Lactose | 9.85% |

The particle size distribution of the batch is a majority for the fractions 25 to 500 $\mu$m.

The relative humidity is 1.9% at the rotary granulation tank outlet.

According to the size of the batches ranging from 1000 to 10,000 g, apparatus GPCG 1 or GPCG 5 from the company Glatt with a rotor tank mounting [lacuna].

EXAMPLE 3

Three-layer effervescent microspheres containing ascorbic acid (vitamin C)

Three-layer effervescent microspheres are manufactured, comprising an alkaline core isolated from the acidic active principle, ascorbic acid, by means of a film of PVP.

| FORMULATION | COMPONENT | PERCENTAGE |
|---|---|---|
| Powder A | | |
| Alkaline compound | Sodium bicarbonate | 25% |
| Binder | PVP K30 | 1.316% |
| Diluent | Lactose | 7.950% |
| Water-soluble isolating agent | PVP K30 | 6.958% |
| Powder B | | |
| Acidic compound Active principle | Ascorbic acid | 50% |
| Flavoring | Orange flavoring | 1% |
| Sweeteners | Sodium saccharinate | 0.2% |
| | Citric acid | 1% |
| Diluent | Lactose | 6.950% |

The test is carried out in apparatus of GPCG1 type from the company Glatt, with the rotor tank mounting.

1460 g of ethanol at 60% by volume are sprayed in total during the three steps, at an average flow rate of 15 grams per minute.

The size of the final batch is 1000 g.

The working yield corresponding to the fraction of particles between 200 and 1000 µm is 65%. The relative humidity is 1.5% at the tank outlet.

What is claimed is:

1. Process for preparing multilayer effervescent microspheres containing an acidic substance, a basic substance, and a water-soluble isolating agent which upon dissolution in water leads, after almost immediate effervescence, to a solution or a homogeneous dispersion of active principle(s), wherein the acidic and basic substances contain or consist of active principle(s), which employs the method of rotary granulation in a fluidized air bed.

2. Process for preparing microspheres defined in claim 1, which employs the method of rotary granulation in a fluidized air bed combined with a system for spraying powder and a system for the tangential spraying of wetting liquid, which comprises two continuous steps, a first step of spheronization of microspheres using a powder A and a second step of spheronization of a powder B on the microspheres of powder A, one of the powders A and B being acidic and the other alkaline.

3. Process according to claim 2, wherein the powder A is introduced directly into the rotary granulation tank and then sprayed with a wetting liquid containing the water-soluble isolating agent, while the powder B and a wetting liquid containing the water-soluble isolating agent are simultaneously and respectively sprayed via the system for spraying powder and the system for the tangential spraying of liquid.

4. Process according to claim 3, wherein the microspheres obtained have an average particle size of between 20 and 500 µm.

5. Process for preparing microspheres as defined in claim 1, which employs the method of rotary granulation in a fluidized air bed combined with a system for the tangential spraying of wetting liquid, which comprises three continuous steps, a first step of spheronization of microspheres using a powder A, a second step of spheronization of a water-soluble isolating agent on the microspheres of powder A, and then a third step of spheronization of a powder B on the microspheres A protected with a film of water-soluble isolating agent, one of the powders A and B being acidic and the other alkaline.

6. Process according to claim 5, wherein the powder A and the water-soluble isolating agent are sprayed with an alcoholic or aqueous-alcoholic solution.

7. Process according to claim 5, wherein the powder B contains the water-soluble isolating agent and is sprayed with an alcoholic or aqueous-alcoholic solution.

8. Process according to claim 5, wherein the powder B is sprayed with a wetting liquid containing the water-soluble isolating agent.

9. Process according to claim 5, wherein the microspheres obtained have an average particle size of between 200 and 1000 µm.

10. Process according to claim 3, wherein the wetting liquid containing the water-soluble isolating agent is polyvinylpyrrolidone dissolved in an alcohol or an aqueous-alcoholic mixture, which is polyvinylpyrrolidone dissolved to 4% by weight in ethanol at 60% by volume.

11. Process according to claim 2 or 5, wherein the powder of alkaline nature contains a sodium bicarbonate or another carbonate used in the preparation of effervescent forms, selected from lithium hydrogen carbonate, monosodium carbonate, lithium glycine carbonate, monopotassium carbonate, calcium carbonate, magnesium carbonate; and one or more active principles and having alkaline properties.

12. Process according to claim 2 or 5, wherein the powder of acidic nature contains citric acid or ascorbic acid or, acetylleucine, and/or one or more, active principles having acidic properties.

13. Process according to claim 1, wherein the powder of alkaline nature also contain an edible diluent and; flavorings and sweeteners.

14. Process according to claim 2 or 5, wherein the microspheres obtained contain 5 to 75% of alkaline substance, 10 to 75% of acidic substance, 3 to 15% of water-soluble isolating agent, 5 to 50% of diluent, and 1 to 30% of flavorings and sweeteners.

15. Process according to claim 2 or 5, wherein the powder A is of alkaline nature and the powder B of acidic nature.

16. Process according to claim 2 or 5, wherein the powder A is of acidic nature and the powder B of alkaline nature.

17. Process according to claim 3 or 6, wherein the wetting liquid is sprayed by means of a nozzle 1.2 mm in diameter, at an average flow rate of between 10 and 30 g/min.

18. Process according to claim 2 or 5, wherein the air inlet temperature of the fluidized bed is between 55 and 65° C. during spheronization steps, and between 75 and 85° C. during drying phases associated with the spheronization steps.

19. Process according to claim 2 or 5, wherein the relative humidity of the microspheres obtained is between 1 and 2% at the rotary granulation tank outlet.

20. Process for preparing microspheres as defined in claim 1, which employs the mounting technique combined with a system for the tangential spraying of wetting liquid.

21. Process according to claim 20, wherein the powder A and the powder B are mounted successively on spheres of active principle coated with water-soluble isolating agent, or on neutral spheres.

22. Process according to claim 12, wherein the powder of acidic nature also contains an edible diluent and flavorings and sweeteners.

* * * * *